United States Patent [19]

Lösel et al.

[11] 4,031,212
[45] June 21, 1977

[54] 3β-(4-OXO-α-L-RHAMNOSYL)-β-HYDROXY-BUFA-4,20,22-TRIENOLIDE

[75] Inventors: Walter Lösel, Ingelheim am Rhein; Werner Traunecker, Munster-Sarmsheim; Wolfgang Hoefke, Budenheim, all of Germany

[73] Assignee: Boehringer Ingelheim GmbH, Ingelheim am Rhein, Germany

[22] Filed: July 30, 1975

[21] Appl. No.: 600,500

[30] Foreign Application Priority Data

Aug. 5, 1974 Germany .......................... 2437612

[52] U.S. Cl. .................... 424/182; 536/5; 536/6
[51] Int. Cl.² ........................... A61K 31/58
[58] Field of Search ............... 260/210.5; 424/182; 536/5

[56] References Cited
UNITED STATES PATENTS 3,783,149  1/1974  Heider et al. ................... 260/210.5

FOREIGN PATENTS OR APPLICATIONS 2,042,075  3/1972  Germany .......................... 260/210.5

*Primary Examiner*—Johnnie R. Brown
*Attorney, Agent, or Firm*—Hammond & Littell

[57] ABSTRACT

The compound of the formula

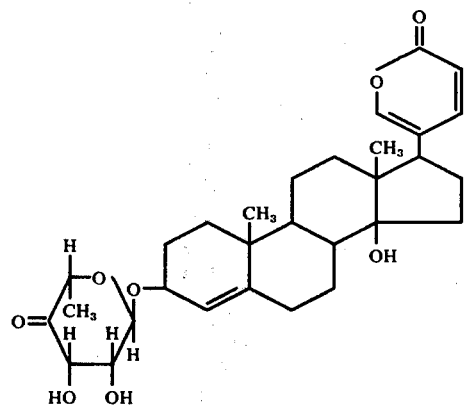

which is useful as a cardiotonic.

3 Claims, No Drawings

3β-(4-OXO-α-L-RHAMNOSYL)-β-HYDROXY-BUFA-4,20,22-TRIENOLIDE

This invention relates to the novel compound 3β-(4'-oxo-α-L-rhamnosyl)-14β-hydroxy-bufa-4,20,22-trienolide, and to a method of preparing this compound.

More particularly, the present invention relates to the novel compound of the formula

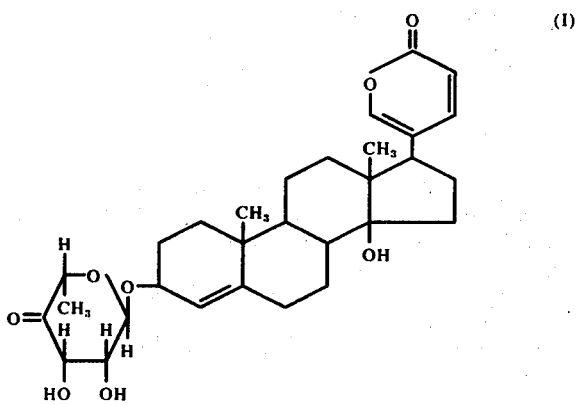

which may be prepared by hydrolysis of a compound of the formula

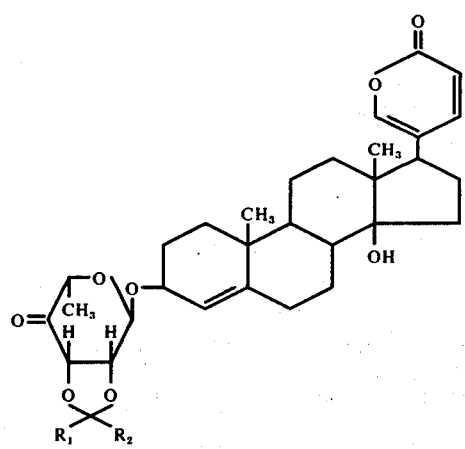

wherein
$R_1$ is hydrogen or lower alkoxy, and
$R_2$ is lower alkoxy, or
$R_1$ and $R_2$ together are oxygen.

The hydrolysis is effected by means of known procedures, preferably with a dilute acid or base, at room temperature or moderately elevated temperatures, and advantageously in an inert organic solvent.

A starting compound of the formula II may be obtained by means of a two-step reaction sequence from proscillaridin A; that is, by reacting the latter with a tetraalkyl orthocarbonate or with an active carbonic acid derivative, such as 1,1'-carbonyl-diimidazole, benzylimidazole-N-carboxylate, chlorocarbonate, phosgene or pyrocarbonate, in the presence of an acid-binding agent, if necessary, followed by oxidation of the hydroxyl group in the 4'-position with dimethylsulfoxide in the presence of dicyclohexyl-carbodiimide and pyridinium chloride.

The following example illustrates the present invention and will enable others skilled in the art to understand it more completely. It should be understood, however, that the invention is not limited solely to the particular examples given below.

EXAMPLE 1

3β-(4'-Oxo-α-L-rhamnosyl)-14β-hydroxy-bufa-4,20,22-trienolide

A mixture consisting of 3.01 gm (5 millimols) of 3β-(2',3'-dimethoxymethylidene-4'-oxo-α-L-rhamnosyl)-14β-hydroxy-bufa-4,20,22-trienolide and 1 ml of 2 N hydrochloric acid was stirred at room temperature for 30 to 60 minutes. The completion of the reaction was ascertained by thin-layer chromatography. After the reaction had gone to completion, the reaction solution was diluted with 100 ml of water and then extracted twice with 50 ml of ethyl acetate each. The combined organic extract solutions were mashed with water, dried over sodium sulfate and evaporated to dryness. The residue was taken up in 50 ml of methanol, the solution was admixed with 3 ml of aqueous 1 M sodium bicarbonate, and the mixture was stirred for about 5 minutes at 30° C. After the reaction had gone to completion (thin-layer chromatographic comparison), the mixture was neutralized in the acetic acid, the reaction solution was concentrated by evaporation to a small volume, and the residue was taken up in a mixture of water and ethyl acetate. The organic phase was separated, dried with sodium sulfate and evaporated to dryness, and the residue was purified by chromatography on a silicagel column (grain size 0.2 – 5.0 mm) with a mixture of chloroform and acetone (3:1) as the eluant. 1.76 gm (66% of theory) of 3β-(4'-oxo-β-L-rhamnosyl)-14β-hydroxy-bufa-4,20,22-trienolide, an amorphous substance having a melting point range of 142°–145° C, were obtained.

The same compound was obtained by acid hydrolysis (2 N hydrochloric acid) of 5 millimols of 3β-(2',3'-ethoxymethylidene-4'-oxo-α-L-rhamnosyl)-14β-hydroxy-bufa-4,20,22-trienolide, or by alkaline hydrolysis (1 M sodium bicarbonate) of 3β-(2',3'-cyclocarbonyl-4'-oxo-β-L-rhamnosyl)-14β-hydroxy-bufa-4,20,22-trienolide.

The compound of the present invention has useful pharmacodynamic properties. More particularly, the compound of this invention exhibits cardiotonic, especially positive inotropic, activities in the isolated ventricle of the guinea pig heart and the heart-lung preparation, and is therefore useful for the treatment of cardiac insufficiencies in warm-blooded animals. The compound is particularly superior over proscillaridin in that its absorption rate is significantly higher than that of the known cardiac glycoside.

In addition, by virtue of the reaction oxo-group on the rhamnose moiety, the compound of this invention is useful as an intermediate for the preparation of other cardiac glycoside derivatives.

For pharmaceutical purposes the compound according to the present invention is administered to warm-blooded animals perorally or parenterally as an active ingredient in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective cardiotronic dosage unit of the compound according to the present invention is from 0.00083 to 0.084 mgm/kg body weight, preferably from 0.002 to 0.034 mgm/kg body weight.

The following examples illustrate a few pharmaceutical dosage unit compositions comprising the compound of the present invention as an active ingredient and represent the best modes contemplated of putting the invention into practical use. The parts are parts by weight unless otherwise specified.

EXAMPLE 2

| | | |
|---|---:|---|
| 3β-(4'oxo-α-L-rhamnosyl)-14β-hydroxy-bufa-4,20,22-trienolide | 0.25 | parts |
| Lactose | 87.75 | " |
| Potato starch | 30.0 | " |
| Gelatin | 3.0 | " |
| Magnesium stearate | 1.0 | " |
| Total | 120.0 | parts |

Preparation

The glycoside is intensively milled with ten times its weight of lactose, the milled mixture is admixed with the remaining amount of the lactose and the potato starch, the resulting mixture is moistened with an aqueous 10% solution of the gelatin, the moist mass is forced through a 1.5 mm-mesh screen, and the resulting granulate is dried at 40° C. The dry granulate is again passed through a 1 mm-mesh screen, admixed with the magnesium stearate, and the composition is compressed into 120 mgm-tablets in a conventional tablet making machine. Each tablet contains 0.25 mgm of the glycoside and is an oral dosage unit composition with effective cardiotonic action.

EXAMPLE 3

Coated Pills

The pill core composition is compounded from the following ingredients:

| | | |
|---|---:|---|
| 3β-(4'-oxo-α-L-rhamnosyl)-14β-hydroxy-bufa-4,20,22-trienolide | 0.25 | parts |
| Lactose | 32.25 | " |
| Corn starch | 15.00 | " |
| Polyvinylpyrrolidone | 2.00 | " |
| Magnesium stearate | 0.50 | " |
| Total | 50.00 | parts |

Preparation

The glycoside is intensively milled with ten times its weight of lactose, the milled mixture is admixed with the remainder of the lactose and the corn starch, the mixture is moistened with an aqueous 15% solution of the polyvinylpyrrolidone, the moist mass is forced through a 1 mm-mesh screen, and the resulting granulate is dried at 40° C and again passed through the screen. The dry granulate is admixed with the magnesium stearate, and the resulting composition is compressed into 50 mgm-pill cores which are subsequently coated in conventional manner with a thin shell consisting essentially of a mixture of sugar and talcum and finally polished with beeswax. Each coated pill contains 0.25 mgm of the glycoside and is an oral dosage unit composition with effective cardiotonic action.

EXAMPLE 4

Drop Solution

The solution is compounded from the following ingredients:

| | | |
|---|---:|---|
| 3β-(4'-oxo-α-L-rhamnosyl)-14β-hydroxy-bufa-4,20,22-trienolide | 0.0125 | parts |
| Saccharin sodium | 0.3 | " |
| Sorbic acid | 0.3 | " |
| Ethanol | 30.0 | " |
| Flavoring | 1.0 | " |
| Distilled water q.s.ad | 100.0 | " |

Preparation

The glycoside and the flavoring are dissolved in the ethanol, and the sorbic acid and the saccharin sodium are dissolved in the distilled water. The two solutions are uniformly admixed with each other, and the mixed solution is filtered until free from suspended matter. 1 ml of the filtrate contains 0.125 mgm of the glycoside and is an oral dosage unit composition with effective cardiotonic action.

EXAMPLE 5

Hypodermic Solution

The solution is compounded from the following ingredients:

| | | |
|---|---:|---|
| 3β-(4'-oxo-α-L-rhamnosyl)-14β-hydroxy-bufa-4,20,22-trienolide | 0.25 | parts |
| Polyethyleneglycol 600 | 700.0 | " |
| Tartaric acid | 150.0 | " |
| Distilled water q.s.ad | 3000.0 | " by vol. |

Preparation

The tartaric acid, the polyethyleneglycol and the glycoside are successively dissolved in a sufficient amount of distilled water, and the resulting solution is diluted with distilled water to the indicated volume and then filtered until free from suspended matter. The filtrate is filled into white 3 ml-ampules in an atmosphere of nitrogen, which are then sterilized for 20 minutes at 120° C and sealed. Each ampule contains 0.25 mgm of the glycoside, and the contents thereof are an injectable dosage unit composition with effective cardiotonic action.

EXAMPLE 6

Suppositories

The suppository composition is compounded from the following ingredients:

| | | |
|---|---:|---|
| 3β-(4'-oxo-α-L-rhamnosyl)-14β-hydroxy-bufa-4,20,22-trienolide | 0.25 | parts |
| Lactose | 4.75 | " |
| Suppository base (e.g. cocoa butter) | 1695.0 | " |
| Total | 1700.0 | parts |

Preparation

The glycoside and the lactose are admixed, and the mixture is milled. The milled mixture is uniformly stirred with the aid of an immersion homogenizer into the suppository base, which had previously been melted and cooled to 40° C. The resulting composition is cooled to 37° C, and 1700 mgm-portions thereof are poured into cooled suppository molds and allowed to harden therein. Each suppository contains 0.25 mgm of the glycoside and is a rectal dosage unit composition with effective cardiotonic action.

The amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. $3\beta$-(4'-Oxo-$\alpha$-L-rhamnosyl)-14$\beta$-hydroxy-bufa-4,20,22-trienolide.

2. A cardiotonic pharmaceutical dosage unit composition consisting essentially of an inert pharmaceutical carrier and an effective cardiotonic amount of the compound of claim 1.

3. The method of increasing the strength of the heart muscle contraction in a warm-blooded animal in need of such treatment, which comprises administering to said animal a composition of claim 2.

* * * * *

UNITED STATES PATENT OFFICE
CERTIFICATE OF CORRECTION

Patent No. 4,031,212          Dated June 21, 1977

Inventor(s) WALTER LOSEL; WERNER TRAUNECKER; WOLFGANG HOEFKE

It is certified that error appears in the above-identified patent and that said Letters Patent are hereby corrected as shown below:

Col. 2, line 32 - "(4'-oxo-$\beta$-L-" should read -- (4'-oxo-$\alpha$-L- --

Col. 2, line 41 - " oxo-$\beta$-L- " should read -- oxo-$\alpha$-L- --

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*